United States Patent [19]

Bednarski et al.

[11] Patent Number: 5,510,481
[45] Date of Patent: Apr. 23, 1996

[54] SELF-ASSEMBLED MOLECULAR FILMS INCORPORATING A LIGAND

[75] Inventors: Mark D. Bednarski; Troy E. Wilson, both of Berkeley, Calif.; Mark S. Mastandra, Brookline, Mass.

[73] Assignee: The Regents, University of California, Oakland, Calif.

[21] Appl. No.: 146,485

[22] Filed: Oct. 29, 1993

Related U.S. Application Data

[63] Continuation of Ser. No. 617,988, Nov. 26, 1990, abandoned.

[51] Int. Cl.$^6$ .......... C07H 15/04; C07H 15/00; C07H 23/00; B32B 9/04
[52] U.S. Cl. .......... 536/120; 536/1.11; 536/4.1; 536/18.4; 536/18.5; 536/18.6; 536/122; 106/287.12; 106/287.13; 428/447; 428/448
[58] Field of Search .......... 536/1.11, 17.1, 536/18.5, 18.6, 18.4, 4.1, 120, 122; 524/58; 106/287.12, 287.13

[56] References Cited

U.S. PATENT DOCUMENTS

| | | | |
|---|---|---|---|
| 3,983,299 | 9/1976 | Regnier | 428/405 |
| 4,702,773 | 10/1987 | Ashlock et al. | 106/287.12 |
| 4,704,416 | 11/1987 | Eck et al. | 524/17 |
| 4,859,538 | 8/1989 | Ribi | 428/474 |
| 4,871,837 | 10/1989 | Magnusson et al. | 536/4.1 |
| 5,051,129 | 9/1991 | Cuthbert et al. | 106/2 |
| 5,112,393 | 5/1992 | Engel et al. | 106/2 |
| 5,156,810 | 10/1992 | Ribi | 422/82 |
| 5,219,652 | 6/1993 | Shimaski | 428/323 |

FOREIGN PATENT DOCUMENTS

| | | |
|---|---|---|
| 0279623 | 8/1988 | European Pat. Off. |
| 2629827 | 10/1989 | France |
| 58168056 | 10/1983 | Japan |
| 04085541 | 3/1992 | Japan |

OTHER PUBLICATIONS

Koontz et al. U.S. patent application Ser. No. 07/857,901.
Matsandrea et al. *J. Mat. Ed.* vol. 11 pp. 529–564, (1989).
Matsandrea et al. *Mat. Res. Soc. Symp. Proc.* vol. 174, pp. 277–288, (1990).

*Primary Examiner*—Douglas W. Robinson
*Assistant Examiner*—Howard C. Lee
*Attorney, Agent, or Firm*—Kathleen Dal Bon; Paul R. Martin

[57] ABSTRACT

Functionalized monomers are presented which can be used in the fabrication of molecular films for controlling adhesion, detection of receptor-ligand binding and enzymatic reactions; new coatings for lithography; and for semiconductor materials. The monomers are a combination of a ligand, a linker, optionally including a polymerizable group, and a surface attachment group. The processes and an apparatus for making films from these monomers, as well as methods of using the films are also provided.

1 Claim, 4 Drawing Sheets

SELF-ASSEMBLED MOLECULAR FILMS INCORPORATING A LIGAND

REFERENCE TO GOVERNMENT GRANT

The United States Government has certain rights to this invention pursuant to Contract No. DE-AC03-76SF00098 between the U.S. Department of Energy and the University of California for the operation of Lawrence Berkeley Laboratory.

This application is a continuing application from the application entitled "SELF-ASSEMBLED MOLECULAR FILMS INCORPORATING A LIGAND" filed Nov. 26, 1990, Ser. No. 08/617,988, now abandoned.

FIELD OF THE INVENTION

This invention relates to the construction of a functionalized monomer that can be assembled into a film that imparts to the surface of materials desired properties. More particularly, the films are fabricated to present ligands at the film surface which are free to interact with specific target molecules thereby influencing the properties of the surface and allowing for the detection of changes in these properties.

BACKGROUND OF THE INVENTION

Certain molecules when placed in contact with a surface can aggregate to form well-ordered two dimensional arrays. This process is called molecular self-assembly (MSA), and it is emerging as an important method to control the interactions between a surface and its environment (interfacial properties). Molecular self-assembly uses the fundamental forces between molecules (Van der Waals interactions, hydrophobic effects and hydrogen bonding) to form highly ordered macromolecular systems. This process has previously been used to synthesize molecular films on a variety of surfaces including gold (Bain and Whitesides (1988) *Science* 240:62–63), alumina (Holmes-Farley (1988) *Langmuir* 4:766–774), platinum (Soriaga and Hubbard (1982) *J Am Chem Soc* 104:3937–3945), and silicon (Maoz and Sagiv (1987) *Langmuir* 3:1045–1051) using commercially available alkylthiols, alkylsulfides, and organosilicon compounds.

Molecular films may be formed on solid supports by a variety of means including covalent attachment such as, for example, alkylsilanes to the surface oxide of silicon surfaces (Wasserman and Whitesides (1989) *Langmuir* 5:1074); by coordinating molecules such as alkylthiols on gold (Netzer et al (1982) *Thin Solid Films* 99:235–241); and by Langmuir-Blodgett (LB) methodology wherein molecules are held together by hydrophobic effects.

Simple chemical modifications of a monomeric subunit contained in a molecular film can lead to changes in the surface properties of the aggregated monomers. These films can be used to investigate and control the adhesive, recognition, wetting, electrochemical, and non-linear optical properties of the material's surface (Swalen et al (1987) *Langmuir* 3:932–950).

To date, general methods to synthesize materials with complex molecules, such as nucleic acids, peptides and carbohydrates, at the surface of films are non-existent.

It would be desirable to synthesize molecular films using functionalized molecules containing complex molecules such as, for example, ligands specific for biological receptors or enzymatic targets. It would also be desirable if these ligands could covalently or non-covalently bind to molecules and to a linker optionally having an internal polymerizable group capable of cross-linking to form polymerized films. Similarly, these monomers should be able to bind to surfaces non-covalently or covalently to generate these films. These materials could be used to detect molecular events at an interface comprising molecular recognition events and translate this information into an electrical or optical signal.

SUMMARY OF THE INVENTION

The present invention provides functionalized monomeric subunits which can be used in the fabrication of molecular films. The present compositions are unique because they contain ligands that bind to biological or chemical targets such as, for example, antibodies, bacteria, viruses and enzymes; functional groups that can be used to modify the electrical and optical properties of a surface; and a domain for surface attachment to materials.

More specifically, the present invention provides functionalized monomers useful in the formation of organic films, comprising a surface attachment group capable of attachment to a surface of a material positioned at one end of the monomer, which surface attachment group is covalently bonded to or coordinated to a linker that is attached to a terminal ligand positioned at the other end of the monomer, wherein said linker is of a length effective to separate the terminal ligand from the surface of the material upon attachment of the surface attachment group to the surface.

In one embodiment of the invention, the linker comprises a polymerizable group which can be cross-linked to construct polymerized films covalently or non-covalently attached to the surface of a material.

In other embodiments the invention relates to a method for the ordered assembly of functionalized monomers into a film, said method comprising:

(a) heating a plurality of functionalized monomers using a class of the functionalized monomers described above in a liquid comprising water or water miscible solvents to form a single monolayer, wherein the ligands in the monolayer are oriented in the lower surface of the monolayer (in the water accessible region); and (b) cooling the liquid and the monolayer concurrently with heating step (a) under conditions establishing a thermal gradient to induce and control crystallization of the film.

In yet another embodiment the invention provides a method of crystallizing a plurality of functionalized monomers having polymerizable groups into a crystalline structure in which the ligand of the monomer is oriented in the lower surface with respect to the crystallized structure and wherein the crystallized structure is essentially a two-dimensional film structure with the ligand exposed on a upper surface of the film and the crystallized structure can be subsequently polymerized into a cross-linked structure which retains the orientation of the ligand on said lower surface of the film, said method comprising:

(a) providing a trough having selected length, width and depth dimensions;

(b) associating a heat exchange block with the trough so that heating and/or cooling fluid flowing through the heat exchange block will heat and/or cool the material within the trough;

(c) interposing a heating element between the trough and heat exchange block so that heat developed by the heating element can affect the rate of cooling of material in the trough when the heat exchange block is operated in a cooling mode, wherein said heating element is constructed to provide deferential heating along the length of the heating element;

(d) maintaining a volume of liquid comprising water or a water miscible solvent in the trough within a selected temperature range;

(e) adding a plurality of functionalized monomers to the volume of liquid in the trough to create a monolayer; and (f) crystallizing the monolayer into an essentially two-dimensional film structure having the ligands of the monomer oriented and aligned on an upper surface of the film structure; said crystallizing including (i) cooling the liquid and monolayer by transferring heat from the trough through the heat exchange block and concurrently (ii) introducing heat through the heating element to provide a deferential heating and thus an overall differential gradient of cooling along the length of the trough to facilitate the process of crystallization of the film and preserve the orientation of the ligands entirely along the upper surface of the film structure.

The crystallized film may be transferred onto the surface of materials by lifting the film onto the material under conditions capable of orienting the ligands onto the upper surface of the film and leaving them accessible to the environment.

Both crystallized films and polymerized films are also provided herein.

In another product embodiment the invention provides an apparatus for the ordered assembly of monomeric compositions into a crystallized film, said apparatus comprising:

(a) a trough means for heating and cooling monomeric compositions in a liquid comprising water or a water miscible solvent;

(b) a heat exchange means for heating and/or cooling material contained in the trough means;

(c) a heating element means for providing differential heating along the length of the heating element means, wherein said heating element means is interposed between said trough means and said heat exchange means; and (d) a heat control means for controlling the rate of heat generated by said heating element means.

The invention also provides a process for detecting a chemical, physical or biological event at the surface interface of a film which process comprises assembling the polymerized film described herein onto an electrode array and exposing the film to the element to be detected thereby causing a physical, electrical or optical change in the properties of the film, and detecting the physical, electrical or optical change of the material.

Lastly, the invention provides a microlithography process for fabricating patterns on the surfaces of films, which process comprises scanning the surface of the polymerized film which has been attached to a material, with a scanning probe microscope.

BRIEF DESCRIPTION OF THE DRAWINGS

FIG. 3 shows how heater wire is wound about the glass plate with the coils spaced more closely together at the left hand end and progressively spaced farther apart in the longitudinal direction toward the right hand end to provide a gradient or differential in the rate of heating along the length of the glass plate. The rate of heating as supplied by the glass plate increases progressively from the right hand end to the left hand end.

FIG. 4 is an illustration of the functionalized monomers of the invention.

MODES OF THE INVENTION

A. Description of Functionalized Monomers

Figure 1:
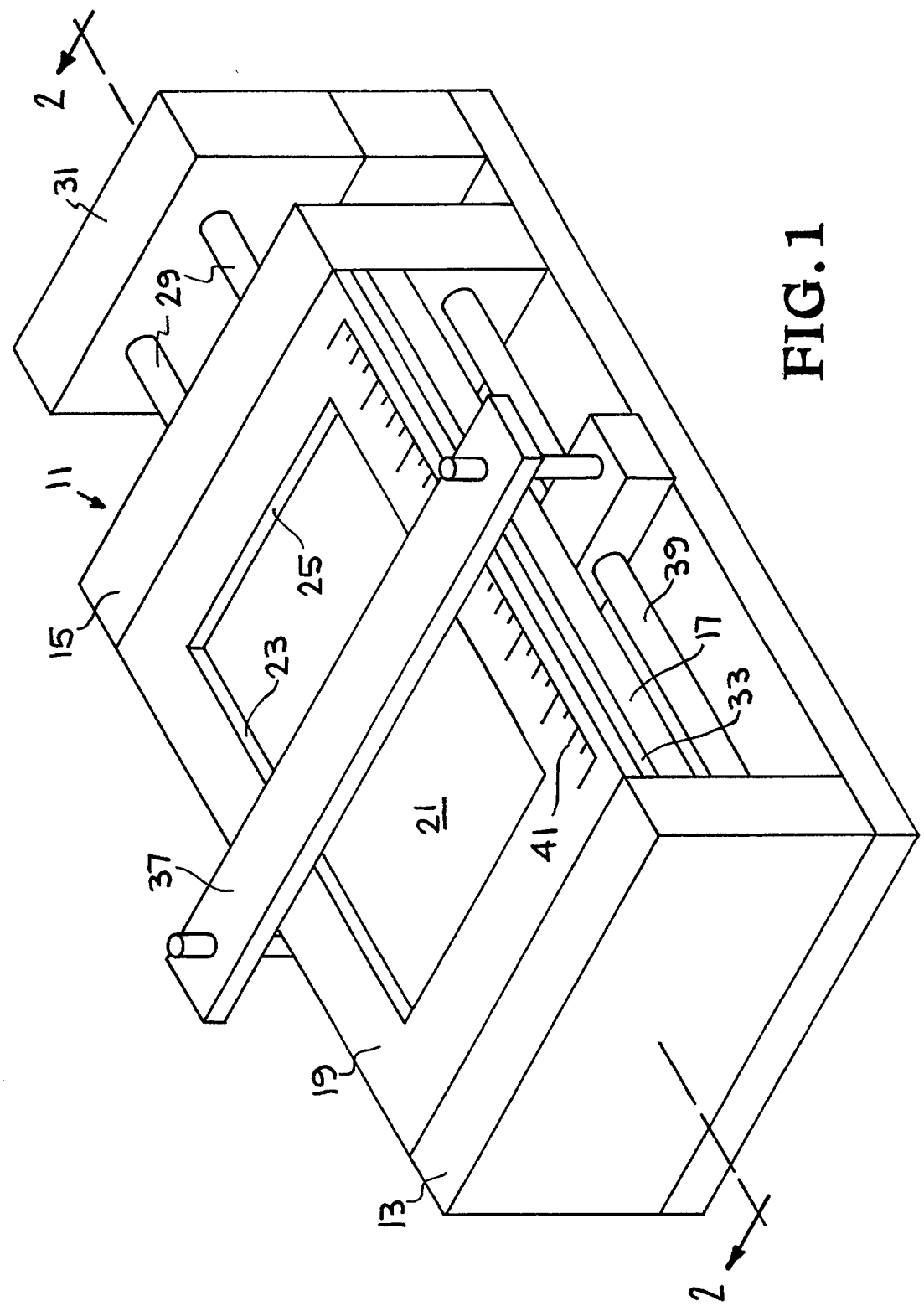
FIG. 1 is an isometric view of a film balance structure for forming two-dimensional crystallized films in which the crystallization has proceeded in accordance with the method of the present invention.

The practice of the present invention will employ, unless otherwise indicated, conventional techniques of organic chemistry, materials science, molecular biology and surface science, which are within the skill of the art. Such techniques are explained fully in the literature. See, e.g., Sambrook et al, MOLECULAR CLONING: A LABORATORY MANUAL, Second edition (1989) and Swalen, et al (1987), supra. All patents and literature citations mentioned herein, both supra and infra, are hereby incorporated by reference.

In describing the present invention, the following terminology will be used in accordance with the definitions set out below.

The first component used to synthesize the compositions of the present invention is a "surface attachment group" used to attach the film to a surface material. Surface attachment groups include chemical compounds which can covalently bind to an attachment site on the surface material and includes without limitation, siloxyanes, preferably trialkoxysilanes, amide groups, esters, disulfide groups, amines and carbamates or thiocarbamates. These surface attachment groups are particularly useful when the surface of the material is hydrophilic, for example, when the surface of the material contains oxides. Materials having oxide surfaces include metals, semi-conducting surfaces such as silicon and gallium arsenide, and insulating materials such as aluminum.

In another embodiment of the invention, surface attachment groups also include chemical compounds which associate with the surface due to hydrophobic effects or form ionic or electrostatic bonds with a surface group such as, for example, lipid-modified molecules which are hydrophobic and associate with other hydrophobic molecules or negatively charged ions that associate with a positively charged surface. As used herein the term "hydrophobic material" includes surfaces which have been treated to render the surface hydrophobic. For example, hydrophobic materials include supports such as modified glass slides, silicon wafers, mica, cellulose acetate, oxidized polystyrene, polyethylene and polyacrylate slides, and metal oxide chips, all of which are materials generally hydrophilic in nature that can be modified to render the surface hydrophobic (Mastandrea et al (1989) *J Mat Ed* 11:529). Other hydrophobic surfaces such as polymer surfaces, Teflon, graphite materials, polystyrene or polyethylene can be used directly for film transfer.

As used herein the term "ligand" refers to a terminal head group molecule which may be biologically reactive with a target molecule or is a chemically competent molecule capable of imparting desired surface characteristics. The ligand can be a polymeric material such as a protein or other polyamino acid, a polynucleic acid including DNA and RNA, or a carbohydrate such as a polysaccharide or a monomeric components thereof such as a single amino acid, a nucleotide or a monosaccharide. Additional ligands may include enzymes, drugs, vitamins and toxins. The ligand may also be a molecule which reacts with a receptor, such as an antibody or a portion of an antibody, which retains the ligand binding capabilities. Typical materials can be taken from any the classes of proteins including without limitation, globulins, albumins, glycoproteins, histones and the like, the tumor markers like CEA (carcinoembrionic antigen) and PAP, the various blood clotting factors and protein hormones including beta-hCG, FSH, LH and prolactin; insulin, thyrotropin, gonadotropin and the like. Examples of polysaccharides include starch, modified monosaccharides such as glucose-1-phosphate, and disaccharides including lactose, and may be derived from microorganisms such as those associated with various species of Salmonella, Streptococcus, and Klebsiella. Other targets include, without limitation, pathogens such as hepatitis A, B and C rubella, the influenza virus, the human immunodeficiency virus and bacterial pathogens including Escherichia, Klebsiella and Salmonella.

The ligand must generally be aligned and oriented above the film surface to allow for interaction with its target receptor molecule. Thus, a "linker" molecule is employed as an intervening spacer. These linkers can be from about 1 to about 50 atoms and especially from about 15 to about 30 atoms long and are generally linear in nature. FIG. 4 illustrates the functionalized monomer of the invention comprising the ligand attached through the linker to the surface attachment group. In one embodiment of the invention, lipids consisting of hydrocarbon chains of about 15 to 30 carbon atoms are used to introduce hydrophobic properties to a region of the functionalized monomer. These lipids may be composed of single or multiple hydrocarbon chains depending on the size of the ligand to be coupled thereto.

The linker may also be comprised of polyether chains, polysulfide chains and polyamine chains having from 1 to 50 atoms, preferably between 15 to 30 atoms.

The linker may also include a polymerizable group. A "polymerizable group" as used herein refers to a region in the linker capable of cross-linking with other monomers when treated under suitable conditions (for example, by heat or by irradiation using ultraviolet light). Polymerizable groups include, without limitation, acetylenes having from 1 to 5 acetylene units, olefins or polyolefins and alpha, beta-unsaturated carbonyl groups. In one embodiment of the invention the polymerizable groups possesses physical, optical and/or electrical properties which permit visual confirmation of the polymerization process. For example, when diacetylene is used as the polymerizable group, the process of cross-linking forms alkene-alkyne linkages which are highly fluorescent and can be used to assay the polymerization and film formation process.

In one embodiment of the invention, the ligand may be optionally labeled with a labelling reagent. The label allows a signal to be measured (preferably quantifiable) when the ligand reacts with its target. Labels may provide signals detectable by fluorescence, radioactivity, colorimetric, X-ray diffraction or absorption, magnetism, diffraction, enzymatic activity and the like.

Figures 4A, 4B:
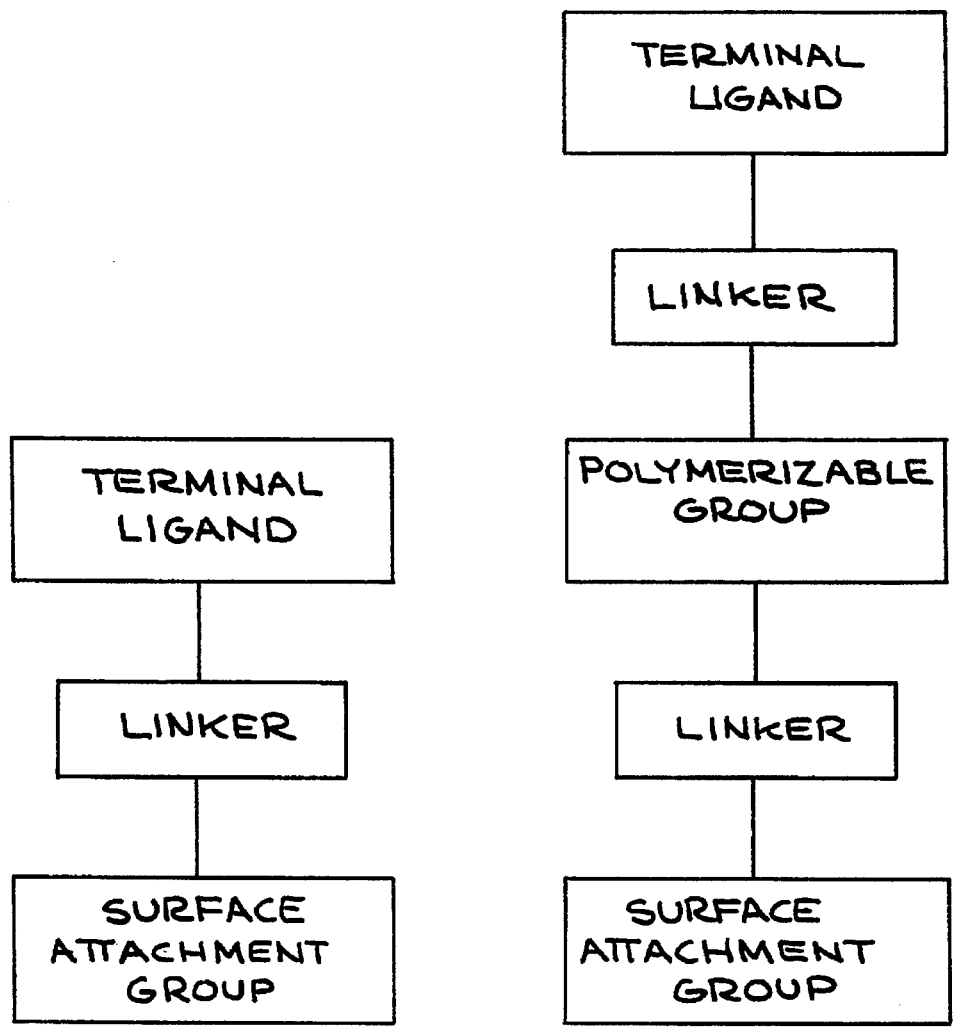
FIG. 4A illustrates the basic monomer having a terminal ligand bound through a linker to a surface attachment group.
FIG. 4B is another embodiment of the functionalized monomer showing a polymerizable group as part of the linker.

The polymerizable group may be interposed within the linker as shown in FIG. 4B or may be placed at either end of the linker depending on the surface attachment group or terminal ligand as the case may be.

The linker as defined must contain functional end groups which bind either covalently or non-covalently to a surface attachment group and the ligand.

To bind the linker to the terminal ligand requires a ligand binding group. As used herein a "ligand binding group" may take the form of a simple bond such as, for example, an amide bond, an aminde bond, an ester or thioester bond, an ether bond, a disulfide bond, a carbamate or thiocarbamate, a methylene bond or any combination of the above. The particular ligand binding group will depend on the choice of the linker and ligand used as would be known to those of skill in the art.

A "surface attachment group" may be required to bind or coordinate the linker to the surface of a material. If the linker is to be covalently bonded to the surface of a material, such surface attachment groups include, without limitation, siloxanes, particularly trialkoxysilanes, amide bonds, amine bonds, ester bonds, disulfide bonds and carbamate or thiocarbamate bonds. Alternatively the linker may be coordinated to the surface of the material. The linker itself may serve as the surface attachment group such as, for example, when the linker is composed of a hydrocarbon chain and the surface of the material is also hydrophobic or treated to possess a hydrophobic environment. In addition the surface attachment group may be an ionic group, a phosphate group or a carboxylic acid bonded by an ionic bond to a positively charged group such as an amine or a metal.

Process and Apparatus for Producing Crystallized Films

A film balance structure for constructing crystalline and polymerized films in accordance with one embodiment of the present invention is indicated generally by the reference numeral 11 in FIG. 1.

The film balance structure 11 shown in FIG. 1 includes two supports 13 and 15. In a specific embodiment of the present invention these supports are made of aluminum.

A copper block 17 is supported between the supports 13 and 15. The copper block 17 is supported above the floor level by the supports 13 and 15.

Figure 2:
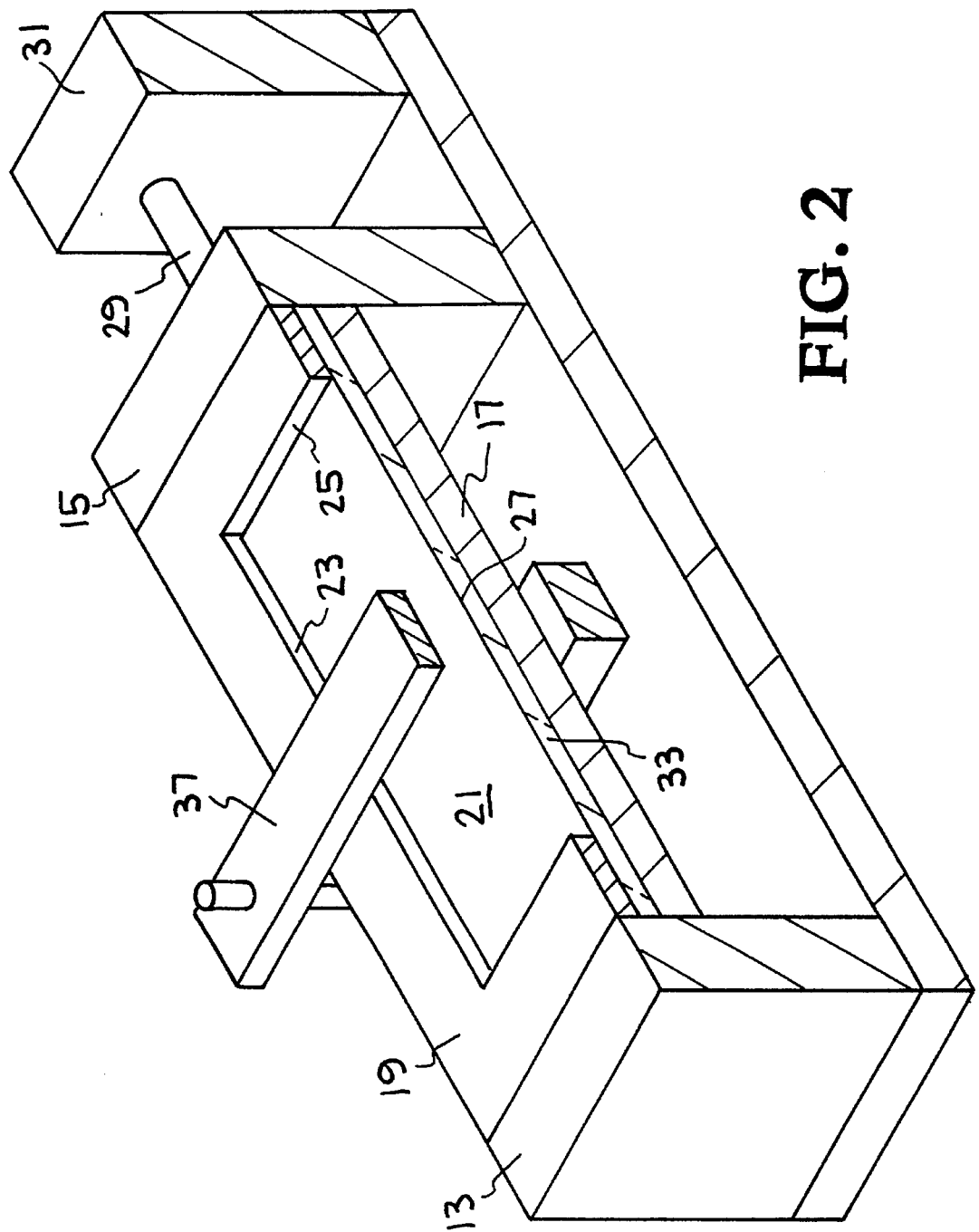
FIG. 2 is an end elevation view, partly broken away in cross section to show details of construction, and taken generally along the line and in the direction indicated by the arrows 2—2 in FIG. 1.

A frame 19 is positioned on top of the heat exchange block 17, as best shown in FIG. 1. As best shown in FIG. 2, the frame has downwardly depending legs which rest along side and upwardly projecting portions of the heat exchange block 17.

The frame 19, in its specific embodiment of the present invention is made of Teflon plastic.

As best shown in FIG. 1 the frame 19 provides a trough 21 having a selected length, width and depth. The trough 21 serves as a reservoir—trough 21 is a fluid type trough for containing the water and functionalized molecules used to make the film in accordance with the present invention. Trough 21 has side walls 23, end walls 25 and a bottom surface 27 (See FIG. 2).

Fluid is circulated through the heat exchange block 17 by a plurality of conduits 29. The circulating fluid heated and cooled by a heater/cooler mechanism 31 according to the sequence of operations to be performed on the material within the trough 21.

As best shown in FIG. 2 a heating element 33 is interposed between the heat exchange block 17 and the bottom surface of the trough 21.

Heating element 33 is a rectangular plate having a length which is essentially the same as the length of the side wall 23 of the trough and having a width which is essentially the same width as the width 25 of the trough so that the plate occupies substantially and entirely the same cross-sectional area as the bottom wall 27 of the trough.

Figure 3:
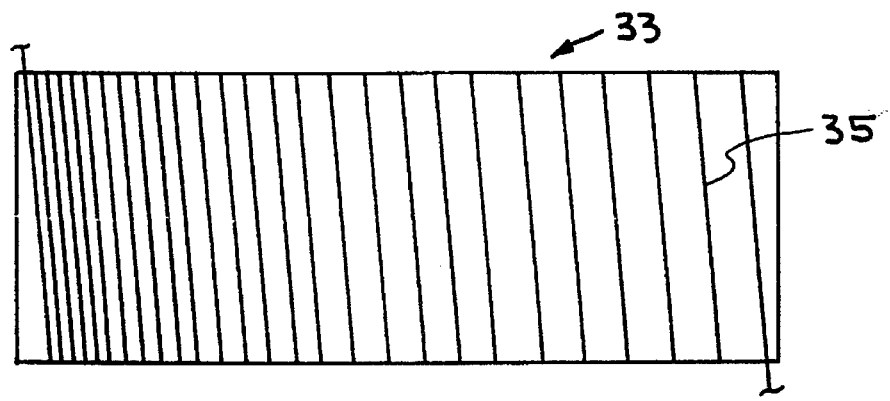
FIG. 3 is a top plan view of a glass plate and heating element incorporated in the film balance structure shown in FIGS. 1 and 2.

In its specific embodiment of the invention the plate is a glass plate. The heating element 33 includes a heater wire 35 which is wound in a helical manner about the width of the plate. The spacing between the turns of the heating wire 35 increases progressively from the left hand end of the plate (as viewed in FIG. 3) to the right hand end of the plate so that the amount of heat transferred from the plate to the trough increases progressively along the length of the plate going from the right hand end of the plate. This progressive increase in the heating produced along the length of the heating element 33 enhances the crystallization and allows the crystallization to proceed as will be described in more detail below. The film balance structure 11 shown in FIG. 1 may also optionally include a while my balance which is a conventional structure for increasing the surface tension on the fluid within the trough 21 and for measuring the actual increased surface tension as produced by the balance.

The Whilemy balance includes a movable pressure bar 37 which is moved along the surface of the liquid in the trough 21 by a actuary arm 39. The frame 19 may optionally have a ruler to measure displacements of the movable pressure bar 37 as it moves along the surface of the liquid.

The Whilemy balance mechanism includes a plate, which is usually a platinum plate and which is suspended from an overhead monitoring unit. As noted above, this Whilemy balance mechanism is an optional mechanism which can be used or which can be omitted in the practice of the process of the present invention.

In operation, the processes of the invention begin by heating the water or water miscible solvent, for example, dimethylformamide (DMF), methanol or dimethylsulfoxide (DMSO), in the trough and maintaining it at a temperature effective to spread the monomers over the liquid surface. Compositions of the present invention comprise both hydrophilic and hydrophobic components. When these compositions are spread over a water surface and their planar density is appropriately increased, they will form a monomolecular film with hydrophilic groups directed downwardly and hydrophobic groups upwardly on the water surface. When the density of molecules on the surface (hereinafter referred to as a planar density) is low, it is "gaseous film." When the planar density of molecules is made higher by increasing surface pressure, the mutual interaction between molecules is intensified, whereby the molecules become "a condensed film" (or a solid film) of a two dimensional solid. This state has high orderliness and uniformity with fairly regular arrangement and orientation of the molecules.

Generally the temperature of the liquid subphase is around 35° to 120° C., more preferably from around 45° to about 85° C. The monomers are added to the water subphase using a microliter syringe in a spreading solution (generally chloroform, hexane or a mixture thereof). The solutions are slowly dropped onto this subphase and allowed to sit for a period of time effective to form a monolayer.

In the second step of the method, the monolayer film is concurrently cooled while heat is still being applied to the water bath. The liquid is cooled by decreasing the liquid temperature to about −10° to about 30° C., more preferably from about 15° to about 25° C. In contrast to conventional crystallization methods which provide uniform cooling of materials in a vertical direction from the bottom to the top of the water bath, the apparatus of the present invention provides a heating element designed to provide deferential heating along the length of the heating element, that is, along the horizontal axis. This horizontal heating gradient progressively induces the crystallization process, facilitating the ordered assembly of the functionalized monomers. The orientation of the ligand is due to the air-surface interface, e.g., the hydrophilic ligand stays in the water.

The temperature gradient induces crystals to form and provides the order which is controllable. This order is essential to the use of these materials in the applications disclosed below.

While the examples provided below use only a single type of functionalized monomer, it is also possible to construct films containing a combination of functionalized monomers both with and without a ligand. This combination of monomers would be useful when the ligand is a large molecule, such as a polypeptide or oligosaccharide, large nucleic acid sequences or when the receptor is large, such as an antibody. To maintain adequate spacing of the polymerizable groups within the film for sufficient polymerization without disturbing the orderliness of the film, these non-ligand containing monomers may also need to be employed.

When the monomer is assembled at an interface and covalently attached to a surface of a material, the monomer may be attached by a procedure reported by Sagiv ((1980) *J Am Chem Soc* 102:92 and (1979) *Isr J Chem* 18:346–353). The monomer (ca. 10 mg) is dissolved in about 25 mL of an organic solvent (e.g., hexadecane, chloroform, ether or a combination thereof) and the surface to be modified is placed in the solution. The surface is then washed using multiple wash cycles with a sufficient amount of chloroform (about 5 mL) and ethanol (about 5 mL) and dried by a stream of nitrogen. These surfaces also use ligands that have protected functional groups which have to be deprotected to be biologically active.

C. Characterization of the Films

A variety of surface-science techniques may be used to characterize the self-assembled organic films of the invention. Many of these techniques are described in Whitesides and Ferguson (1988) *Chemtracts* 1:171–187, which is incorporated herein by reference.

Contact angles are a measurement of the macroscopic surface property of wettability and are used as an indicator of surface hydrophilicity and hydrophobicity. Wettability is sensitive to surface free energy and is quantified by measuring the contact angle at the solid-liquid-vapor interface. Various techniques for measuring contact angles have been reviewed in detail (DeGennes (1985) *Rev Mod Phys* 57:827). This simple measurement can, to a first approximation, determine the degree of nonspecific adhesion of different biological molecules to surfaces. Low contact angles, for example, (hydrophilic surface) seem to promote non-specific adhesion of salmonellae strains, high contact angles (hydrophobic surface) can stop nonspecific adhesion.

The X-ray photoelectron spectroscopy (XPS) technique uses X-rays to eject core electrons from atoms bound at the surface. The relative intensity of these atoms can give information on the type of functional groups present on the material up to about 50 Å. The energy required to eject an electron from an atom is called the binding energy (BE) and is characteristic of each element present at the surface. The XPS spectrometer irradiates the surface with high-energy X-ray photons which collide with surface atoms and eject electrons from the core energy levels. The analyzer subtracts the kinetic energy (KE) of the emitted electrons from the energy of incident X-ray photons (hv) to give the binding energy (BE).

XPS can provide an unambiguous chemical signature of a sample. The peak heights, widths and positions in an XPS spectrum provide more information than simple elemental identification. The shifts in binding energy reflect the oxidation states of surface atoms and allow one to determine chemical groups such as methylene carbons versus the carbon of a carbonyl group.

Elliposometry gives a macroscopic view of the order present in the film by using the difference in the refractive index of the bulk surface versus the refractive index of the monolayer. This method is used to estimate the approximate thickness of molecular films.

Scanning electron microscopy (SEM) is used for analyzing the film at high resolution (about 1 micron). However the film has to be coated with conducting material such as gold or fixed with uranyl acetate to perform these studies.

Fluorescence spectroscopy measures the fluorescence of surface groups. This technique permits one to assay for density of the functionality after covalent attachment of fluorescent probes which may be used independently as the ligand or in combination with a ligand in the derivation of the functionalized monomers of the invention.

Scanning proble microscopy such as scanning tunneling microscopy (STM) and atomic force microscopy (AFM) allow the analysis of surfaces at the submicron level. They can determine the precise nature of the surface and determine exact surface topographical order to relate detailed surface structure information.

D. Industrial Applications of the Films

Films that control the orientation of ligands that can bind to receptors, antibodies and enzymes can be used to detect these events at the film's interface. For example, a carbohydrate group composed of mannose or other saccharide units bind to pathogenic forms of *E. coli* (e.g., K-12) that cause sepsis and meningitis. By attaching to ligands on the surface of films causes physical changes in the film that can be detected by changes in mass on the surface of the film via surface acoustic wave detectors, changes in conductivity, capacitance, fluorescence, or linear and circular dichroism.

When enzymes catalyze reactions that change the surface of the film, the interfacial properties of the film can be detected by methods previously described for receptors. The change in interfacial properties is often reflected in a change in the character of the film.

The films and methods of making the films as described herein are also useful for purposes of quality control. For example, organic solvents and toxins can bind to the surface of the film. These can be detected by the methods previously described. Similarly, organic materials can also insert into the films causing disruption of the film. Characterization of the films using the previously described methods permit such contaminants to be detected.

Another application in the use of the films is in combination with scanning probe microscopies to create lithographic patterns on the surface of materials. This application may be used to write device patterns on the surface of materials in dimensions one to two orders of magnitude smaller than current technology permits. Alternatively, the scanning probe microscopies can be used to polymerize the film, to make indentations on the film and create other patterns to store information on the surface.

The following examples are offered by way of illustration and are not intended to limit the invention in any manner. In these examples all percentages are by weight if for solids and by volume if for liquids, unless otherwise noted, and all temperatures are in degrees Celsius unless otherwise noted.

EXAMPLES

Example 1

Synthesis of Organic Surfaces

A. Cleaning of Wafer

A variety of organic surfaces terminating in simple functional groups (e.g., amines, thiols, esters and lower alkyl chains) with variable linker lengths were synthesized. Organic surfaces (10) through (17) listed in Table 1 were prepared on silicon oxide wafers using techniques similar to those described by Maoz and Sagiv (1987), supra and Haller (1978) *J Am Chem Soc* 100:8050–8055. Briefly, single crystal silicon wafers were protected and then cut into 1×1.5 cm pieces.

Both 2" and 4" diameter Si (100) wafers (p-type, boron doping to 15–30 ohm-cm from Uni-Syl) and 4" Si (111) (p-type, boron doping to 12–20 ohm-cm from Monsanto) have been used with identical results. The water thicknesses are generally between 20 and 25 mM. In all cases, the silicon wafers were prime/electronic grade quality. The silicon surface was protected from cutting damage by spinning a layer of photoresist onto the wafer. The wafer was then scored (using a Tempress diamond saw) into pieces and the resist was removed with acetone.

Any hydrocarbon contamination was removed from the surface to ensure the formation of high quality films. Thus silicon wafers were cleaned by immersion into Teflon containers of $H_2SO_4$ and $H_2O_2$ at 12° C. for 10 min. A solution of concentrated $H_2SO_4$ (1L) and $H_2O_2$ (100 ml) (piranha) was used to effectively oxidize residual carbon at the surface (Bain and Whitesides, (1988) *J Am Chem Soc* 110:6560). The wafer was rinsed thoroughly in flowing deionized water (DI $H_2O$) before immersion into dilute hydrofluoric acid (HF). HF solution was prepared by mixing 49% HF from Aldrich (electronic grade, used as received) with DI $H_2O$ in a ratio of 100:1 ($H_2O$:HF). The weakly oxidizing solution of DI $H_2O$ and $H_2O_2$ (100:1) is kept at 60° C. and the wafers are immersed until they emerge completely wet with water (about 30 sec). The HF solution strips the silicon wafer of the native surface oxide leaving a hydrophobic surface that is thought to be terminated with hydrogen. The wafer was again rinsed with flowing DI $H_2O$ to remove residual HF. Typically, the wafers are immersed in the HF solution only long enough for them to emerge completely dry (about 10–15 sec). The HF solution strips the silicon wafer of the native surface oxide leaving a hydrophobic surface that is thought to be terminated with hydrogen. The wafer was again rinsed with flowing DI $H_2O$ to remove residual HF. The weakly oxidizing solution of DI $H_2O$ and $H_2O_2$ (100:1) is kept at 60° C. and the wafers are immersed until they emerge completely wet with water (about 30 sec). As a final step, the wafers were dried in flowing nitrogen gas in a spin-dryer for 2 minutes.

The unpolished sides of the silicon samples must be metallized with chromium and gold to make an ohmic contact for surface analysis or device fabrication. After the wafers had been completely cleaned of hydrocarbons, they were loaded into a Veeco 401 vacuum evaporator. The Veeco is set-up to perform chromium and gold evaporation sequentially without breaking vacuum. Base pressure on the system is $5\times10^{-7}$ torr and the deposition rate for both metals is approximately 15 Å/s measured with a crystal thin-film detector. Typically, 350 Å of chromium as a primer followed by 1000 Å of gold were used. The wafers were immediately transferred into the desired silylating solution after metal deposition.

B. Silylation of Silicon Surface

This example provides a general protocol for the derivations of silicon surfaces as described in Table 1 below. The silicon wafer was then incubated for 30 minutes in a solution of 3-aminopropyltriethoxysilane (0.05% by volume) suspended in freshly distilled anhydrous ethyl ether in an acid-cleaned petri dish. The surface modification of silicon oxide with a short-chain silane produces a film which completely passivates the surface preventing further silylation. The surface was washed with flowing, DI $H_2O$ for several minutes to remove the excess silane. Finally, the surface was dried in a nitrogen spin-dryer and was ready for characterization and use in derivatization reactions.

It should be noted that a potential problem occurs when the surface is over-exposed to the silane solution. We have observed that over-exposure gives a cloudy surface which we attribute to polymer formation. This problem has also been reported in similar procedures to modify silicon with alkylsilanes (Haller (1978), supra).

The organic surfaces (10) through (17) listed in Table 1 were prepared on the silicon oxide wafers using techniques similar to those described by Sagiv (1980) *J Am Chem Soc* 102:92.

Example 2

Synthesis of Carbohydrate Surfaces

The most easily accessible routes to carbohydrates which are activated for attachment to silicon surfaces was through the hydrosilation of glycosides connected to a hydrocarbon linker that is terminated in an olefin. Olefinic alcohols are readily available and easily attached to glycosyl bromides using the Helfreich-Weis modification of the Koenigs-Knorr reaction (Paulsen and Tietz, (1985) *Angew Chemic Intl Ed Eng* 24:128):

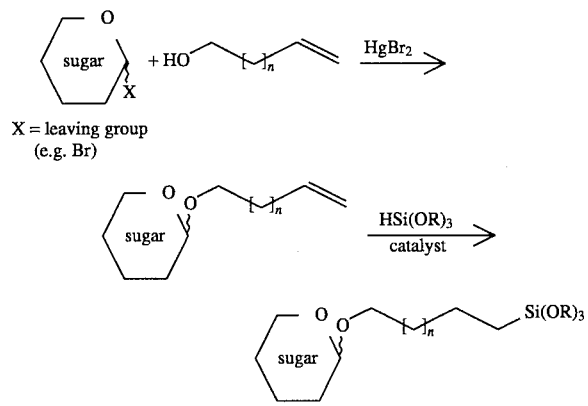

X = leaving group (e.g. Br)

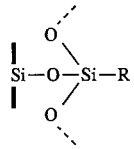

| | Surface (R) | XPS [element: shift (%)] | Contact Angle ($H_2O$) |
|---|---|---|---|
| 10 | ⊢—OH | C: 285.2 (49); O: 533.3 (32) | 15° ± 2° |
| 3 | ⊢∼∼N(H)∼∼N(H)∼NH₂ | C: 287.0 (49); O: 533.2 (26); N: 400.5, 402.3 (19) | 22° ± 2° |
| 11 | ⊢∼∼N=⟨ ⟩N (imidazole) | C: 285.5 (35); O: 532.8 (40); N: 400.2, 401.4 (8) | 25° ± 4° |
| 12 | ⊢∼∼NH₂ | C: 285.9 (47); 5332.2 (33); N: 402.5 (4) | 30° ± 7° |
| 13 | ⊢∼∼CN | C: 287.4, 285.6 (53); O: 533 (26); N: 400.4 (9) | 55° ± 3° |
| 14 | ⊢∼CO₂Me | C: 285.9 (51); O: 533.5 (38) | 63° ± 2° |
| 15 | ⊢∼⟨phenyl⟩—SO₂Cl | C: 284.7 (39); O: 532.1 (35); S: 168.7 (8); Cl: 200.3 (4) | 73° ± 1° |
| 16 | ⊢∼∼SH | C: 286.7, 285.3 (42); O: 532.7 (30); S: 163.9, 165.0 (13) | 80° ± 4° |
| 17 | ⊢—(CH₂)₁₇—CH₃ | C: 285.2 (30); O: 533.2 (44) | 106° ± 2° |

Glycolipids activated at one end for attachment to the surface and terminated in glucose, galactose, and mannose were synthesized. Mannose was chosen because it is known that receptors exist on bacteria that bind to alpha-mannosides. A fluoroglucose derivative was also chosen because the fluorine atom is an excellent label for XPS. This label would help quantify the extent of modification of the surface with the carbohydrate. A glucose surface was synthesized to study the enzymatic transfer of galactose onto the surface by galactosyl transferase and phosphorylation by the use of hexokinase. This approach would allow for further modification of silicon surfaces by enzymatic methods. All monomers were purified by Kugelrohr distillation under reduced pressure until acceptable purity was attained, as determined by $^1$H NMR, $^{13}$C NMR, and elemental analysis. A typical synthetic scheme for the construction of the mannose monomer (7) is outlined below.

A. Synthesis of Triethoxysilylmannoside (7)

Commercially available D-Mannose (1) was acetylated using acetic anhydride in pyridine to give compound (2). Compound (2) was treated with a 30% solution of anhydrous hydrobromic acid in glacial acetic acid to form the acetobromo-alpha-D-mannopyranose (3). Treatment of (3) with 2,6-Lutidine in methanol and chloroform gives the mannose ortho ester (4.) Compound (4) is deacetylated and benzylated using standard procedures to give compound (5). Treatment of (5) with various hydroxy-olefin derivatives using p-toluene sulfonic acid (TsOH) as a catalyst gives alpha-mannosides (6a–d) (n=4,6,8,10). The specific experimental details provided below are for the synthesis of compound (6a).

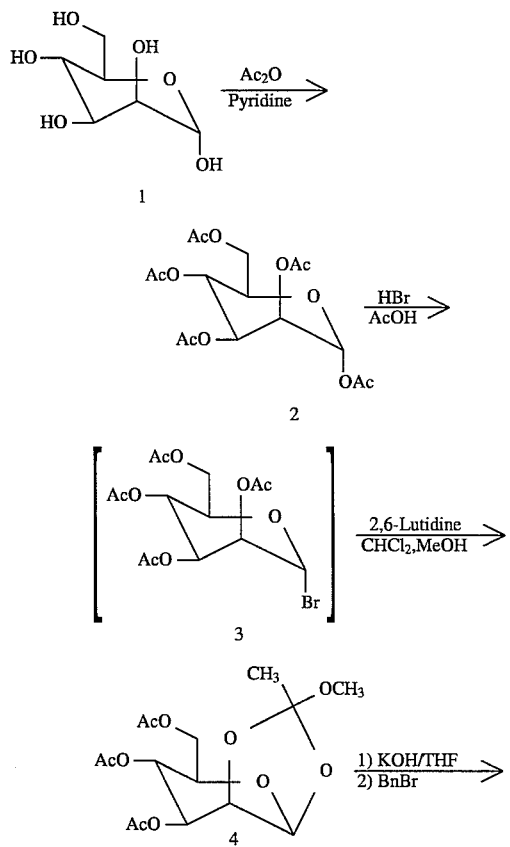

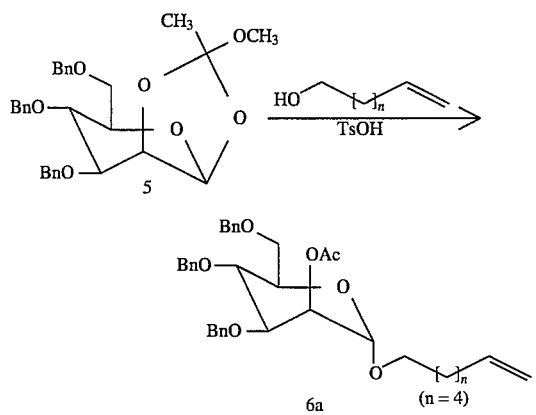

Compound (6a) is debenzylated and deacetylalted using sodium and liquid ammonia (Na/NH$_3$) followed by reacetylation using acetic anhydride in pyredine. Hydrosilation of the olefin using choloplatinic acid (PtCl$_4$.2HCl) and triethoxysilane ((EtO)$_3$SiH) in benzene gives the target molecule compound (7).

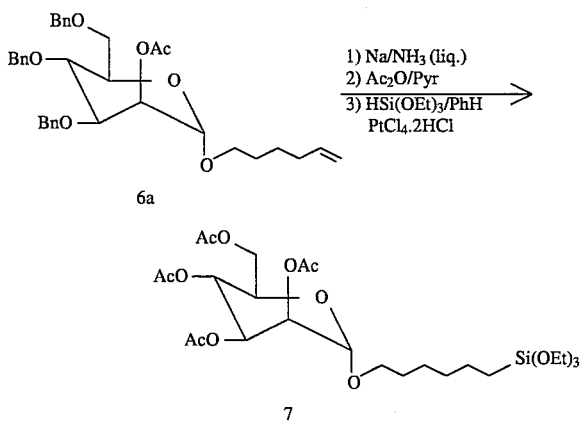

B. Synthesis of carbohydrate modified silicon surfaces (22) and (23)

A typical synthetic scheme for the construction of the mannose surface is outlined below. Surface (22) was prepared by submerging a freshly cleaned wafer in a 2% solution of compound (7) in hexadecane/chloroform/carbon tetrachloride (80:8:12) for 5 minutes. The wafer was rinsed with 5 ml of toluene and 5 ml of absolute ethanol, and dried under a stream of nitrogen.

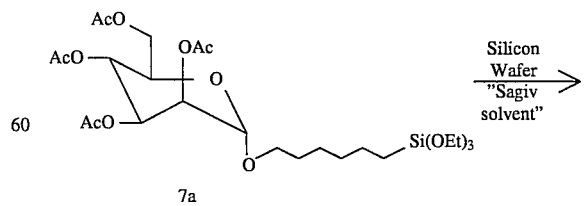

15
-continued

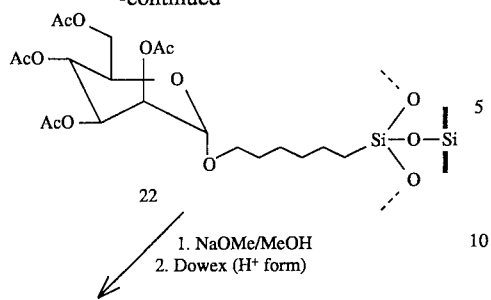

22

1. NaOMe/MeOH
2. Dowex (H+ form)

16
-continued

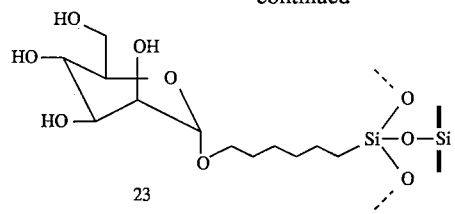

23

The data for surfaces (22) and (23) are given in Table 2.

$$\begin{array}{c} O \\ | \\ Si-O-Si-R \\ | \\ O \end{array}$$

| | Surface (R) | XPS [element: shift (%)] | Contact Angle (H$_2$O) |
|---|---|---|---|
| 18 | AcO-sugar-OAc (triacetate) -O-(CH$_2$)$_n$- | C: 284.5–289.4 (63); O: 532.5 (34) | 32 ± 9° |
| 19 | HO-sugar-OH (trihydroxy) -O-(CH$_2$)$_n$- | C: 285.3–288.4 (53); O: 533.1 (34) | 27 ± 3° |
| 20 | AcO-sugar-OAc -O-(CH$_2$)$_n$- | C: 283.5–289.4 (49); O: 532.5 (37) | 34 ± 2° |
| 21 | HO-sugar-OH -O-(CH$_2$)$_n$- | C: 284.8–288.9 (39); O: 532.7 (45) | 27 ± 2° |
| 22 | AcO-sugar-OAc -O-(CH$_2$)$_n$- | C: 284.4–288.4 (50); O: 532.4 (37) | 53 ± 2 |
| 23 | HO-sugar-OH -O-(CH$_2$)$_n$- | C: 284.4–288.1 (54); O: 532.6 (42) | 42 ± 2 |
| 24 | F-sugar-OAc (fluoro triacetate) -O-(CH$_2$)$_n$- | C: 284.0–289.6 (56); O: 532.6 (33) F: 687.0 (3) | 30 ± 2° |

-continued

|   | Surface (R) | XPS [element: shift (%)] | Contact Angle (H₂O) |
|---|---|---|---|
| 25 | (structure shown) | C: 284.9–289.0 (28); O: 532.6 (46); F: 687.0 (2) | 25 ± 2° |
| 26 | mixed monolayers (17 & 18) | C: 284.6–288.3 (44); O: 532.6 (41) | 105 ± 2° |
| 27 | mixed monolayers (17 & 18) | C: 284.7–288.5 (49); O: 532.5 (47) | 105 ± 2° |

The increase in the contact angle for water on surface (22) from 15°±2° (Compound 10, Table 1) to 32°±2° indicates modification of the surface with compound (7). High resolution XPS spectrum of the carbon region of (22) shows a peak at 289.4 eV, which represents 12% of the total carbon signal and indicates the presence of the carbonyl carbon atoms of the acetate protecting groups on the sugar.

The surface-bound mannose was deprotected by treating (22) with sodium methoxide in methanol for 1 hour followed by neutralization of the solution using Dowex H⁺ resin (Biorad) to give surface (23). This surface showed a reduced water contact angle to 24°±2°, indicating a decrease in hydrophobicity due to the loss of the acetate protecting groups. The XPS spectrum of (23) confirms this result, the carbonyl peak at 289.4 eV disappears. An ellipsometry measurement of surface (23) shows a film thickness of 10.5±2.5 Å which is within experimental error of the expected thickness of the surface.

C. Enzymatic Modification of Surface

Functionalized biological molecules such as complex carbohydrates and oligosaccharides are often difficult to synthesize chemically and attach to surfaces. Thus investigations into the use of enzymes to modify surfaces were investigated. Towards this goal the lactose surface (29) was synthesized by enzymatically attaching galactose to glucose residues on a silicon surface using galactosyl transferase.

PROVIDE EXPERIMENTAL PROTOCOL

Other modifications such as the phosphorylation of a glucose using hexokinase were also accomplished. The alpha-Glc surface was treated with a 1 to 10 mM solution of phosphoenolpyruvate (PEP) in water (pH 7) and a catalytic amount of ATP, hexokinase and pyruvate kinase. The surface was submerged in this solution and allowed to incubate at 37° C. for 24 h. The surface was removed from the solution and washed thoroughly with distilled water. XPS was used to assay the surface for the presence of phosphate on the carbohydrate.

The alpha-Glc was also treated with UDP-Gal (in a 1–10 mM solution in water pH 7) and a catalytic amount of galactosyl transferase was added. The surface was submerged in this solution and allowed to incubate at 37° C. for 24 h. The surface was removed from the solution and washed thoroughly with distilled water. The surface was assayed for reaction by binding to pathogenic organisms as taught below.

These results demonstrate that the enzymatic modification of semiconductor materials is a powerful method to control the interfacial properties of surfaces.

D. Adhesion of Bacteria to Alkyl Surfaces (23–35)

Wild type salmonella typhimurium were grown in M9 minimal medium supplemented with glucose as a carbon

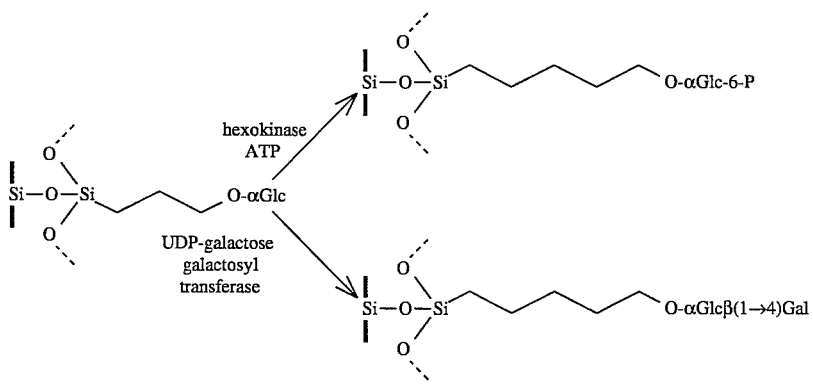

source. This strain was chosen because it expresses type 1 pill which bind to simple alpha-mannosyl glycosides. The cells were harvested in the log phase of growth as determined by the optical density at 620 nm (between 0.5 and 0.6 units), and transferred into a 200 mM phosphate buffer at pH 7.4. This buffer maintains cell life but not cell growth. The cells were diluted to $2.0 \times 10^7$ cells per mL for adhesion experiments.

For adhesion studies surfaces (3) and (10-17) were submerged in the cell suspension for 4–8 hours, after which the surfaces were gently rinsed and blown dry under a stream of nitrogen. The surfaces were coated with gold or osmium tetroxide stain and assayed for adhesion using SEM. Cell density was measured by counting the average number of cells present in 1 $mm^2$.

The data in Table 3 indicate that a relationship exists between the contact angle measurement of the surface and bacterial adhesion. Surface (3) and the underivatized surface (10) all have contact angles of 30° or less, and they show cellular adhesion of 10–5 cells per $mm^2$. The highest degree of adhesion was associated with the underivatized wafer.

Nonspecific adhesion, therefore, seems to occur at contact angles below 35°. The one exception to the rule occurs with sulfonyl chloride surface (15). Here it is possible that the functional hydroxyl groups on the surface of the cell alkylate the sulfonyl groups of (15) to form a covalent bond between the cell and the surface. Whether there is a cutoff point for adhesion based on hydrophobicity (somewhere around contact angle of 30°) or whether the effect is one of surface charge interactions and the nature of functional groups remains to be determined.

E. Adhesion Studies on Carbohydrate Surfaces

Incubation of carbohydrate surfaces (18–27) with cell preparations as described above were also performed. The results are provided in Table 3 below. Surfaces (23) (mannose), (21) (glucose), and (19) (galactose) all showed adhesion to cells, with mannose having the highest degree of cell attachment, followed by galactose and glucose. No adhesion was observed on the protected surfaces (18), (20) and (22).

It is difficult to discern between specific and non-specific adhesion on surfaces (19) and (21) since the contact angles for these surfaces are between 25° and 30° (i.e. in the cutoff range observed for the simple organic surfaces). However, the fact that the cell density on the mannose surface is high and on the glucose surface is low indicates that it is likely that receptor mediated adhesion occurs. To help clarify this issue we synthesized mixed alkyl-mannose surface (27). This surface was composed of the hydrocarbon chains used in the construction of surface (17) and the monomers used to synthesize the mannose surface (23). Despite the high contact angle measurement of surface 27 (0°=105°) strong adhesion of bacteria to the surface was observed. As in previous examples no adhesion was observed on the acetylated surface in the case of surface (26).

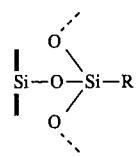

| | Surface (R) | Cell Adhesion |
|---|---|---|
| 10 | ⊢—OH | +++ |
| 3 | ⊢∼∼N(H)∼N(H)∼NH₂ | ++ |
| 11 | ⊢∼∼N=⟨imidazole⟩N | ++ |
| 12 | ⊢∼∼NH₂ | ++ |
| 13 | ⊢∼∼CN | − |
| 14 | ⊢∼∼CO₂Me | − |
| 15 | ⊢∼∼C₆H₄—SO₂Cl | + |
| 16 | ⊢∼∼SH | − |
| 17 | ⊢—(CH₂)₁₇—CH₃ | − |
| 18 | peracetylated sugar-O-alkyl | − |
| 19 | galactose-O-alkyl | + |
| 20 | peracetylated sugar-O-alkyl | − |
| 21 | glucose-O-alkyl | + |
| 22 | peracetylated sugar-O-alkyl | − |
| 23 | mannose-O-alkyl | +++ |

21
-continued

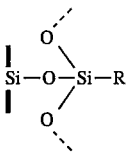

| Surface (R) | Cell Adhesion |
|---|---|
| 24 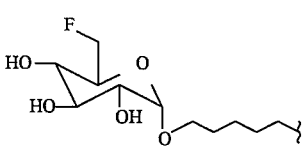 | n/a |
| 25 (structure with F, HO, HO, OH) | n/a |
| 26 mixed monolayers (17 & 18) | − |
| 27 mixed monolayers (17 & 18) | +++ |

− = 0 cells/mm²
+ = 0–10
++ = 10–15
+++ = >15

Example 3

Synthesis of Polymerized Films

A. Synthesis of Funtionalized Monomers
Experimental Section

Triethylamine and acetonitrile were distilled from calcium hydride and used immediately. Dichloromethane was distilled from $P_2O_5$, and ethyl ether was distilled under nitrogen from sodium/benzophenone ketyl. Methanol and dimethyl sulfoxide were HPLC grade from Aldrich and were used as received. Ethanol was 200 proof grade Gold Label from Gold Shield Chemicals. Distilled water was used in all applications. The silical gel used in column chromatography was Universal Absorbents DCC. $^1$H NMR was obtained at 400 or 500 MHz using Brucker superconducting FT NMR spectrometers. $^{13}$CNMR spectra were proton decoupled and were measured at 100.6 MHz on the 400 MHz Brucker spectrometer. Chemical shifts are reported in δ values, positive values indicating shifts downfield from tetramethylsilane. The internal reference for the $^1$H and $^{13}$C NMR spectra obtained in CDCl₃ and CD₃OD was tetramethylsilane, $^1$H NMR spectra are tabulated in order; multiplicity (s, singlet; d, doublet; t, triplet; m, multipier; br, broad; app, apparent), number of protons and coupling constants (reported in Hz). Fast atom bombardment mass spectra (FAB⁺) were obtained with an AE1 M512 mass spectrometer at the Mass Spectometry Facility at U. C. Berkeley.

L-phenylalaninamide (Registry Number 5241-58-7), L-serinamide hydrochloride, L-alaninamide hydrochloride (Registry Number 33208-99-0) and L-glycinamide hydrochloride (Registry Number 1668-10-6) were obtained from Sigma and were used without further purification. N-hydroxysuccinimide (Registry Number 6066-82-6), 1-(3-dimethylaminopropyl)-3-ethylcarbodimide hydrochloride (EDCI) (Registry Number 25952-53-8) and trimethylacetic acid were obtained from Aldrich and were used as received. The 10,12-pentascosadiynoic acid (PDA) (Registry Number 66990-32-7) was purchased from Farchan Laboratories and was purified by dissolution in chloroform or methylene chloride and filtration through glass wool to remove the polymer present in the commercial preparation.

N-hydroxysuccinimide ester of 10,12-pentacosadiynoic acid

To a stirring solution of 250 mL $CH_2Cl_2$ was added 8.81 g of 10,12-PDA (23.6 mmol), 3.04 g of N-hydroxysuccinimide (25.9 mmol) and 5.06 g of EDCI (25.9 mmol). The solution was initially cloudy white, but cleared immediately upon addition of 5 mL triethylamine. The solution was allowed to stir overnight in the dark at 0° C. The solution was evaporated to dryness under reduced pressure (rotary evaporator). Chromatography on silica gel eluting with hexane/CHCl₃/CH₃OH (60:37:3) afforded 10.23 g (21.7 mmol) of the product as a white powdered solid in 92% yield. $^1$H NMR (500 MHz, CDCl₃, 25° C.): δ0.855 (3H, t, J=6.7), 1.23 (26H, br s W $_{1/2}$=20), 1.50 (4H, complex m), 1.71 (2H, complex m), 2.21 (3H, t, J=6.8), 2.56 (3H, t, J=7.7), 2.81 (2H, d, J=2.9); $^{13}$C NMR (CDCl₃); δ14.02, 19.06, 19.08, 22.58, 24.44, 25.49, 28.17, 28.25, 28.58, 28.68, 28.75, 28.79, 29.00, 29.24, 29.37, 29.50, 29.52, 29.54, 30.80, 31.81, 65.14, 65.23, 77.32, 77.46, 168.54, 169.11; high-resolution mass spectrum (FAB⁺) calcd. for $C_{29}H_{45}NO_4$ (MH⁺): 471.3349.Found: 471.3378.

10,12-pentacosadiynoicglycinamide (PDA-glycinamide)

To a stirring solution of 100 mL $CH_2Cl_2$, 50 mL DMF, 50 mL $CH_3CN$ and 20 mL $N(Et)_3$ was slowly added (ca. 1 min) 2.29 g (4.87 mmol) of PDA-NHS and 0.840 g (7.31 mmol) L-glycinamide hypochloride. The solution initially formed a cloudy white suspension which cleared with gentle warming. After stirring for 30 min at 25° C., the resulting solution was extracted three times with 50 mL portions of distilled H₂O. Upon addition of the H₂O, a cloudy while emulsion formed that was cleared by back-extracting the H₂O solution with three 100 mL portions of CHCl₃:hexane (1:1). The three organic fractions were combined and concentrated to dryness under reduced pressure on a rotary evaporator at room temperature. The crude yield for the reaction was 1.91 g (91% crude yield), and a pure product was obtained by recrystallized from 75 mL of CH₃OH to give 1.72 g of a white crystalline solid (3.99 mmol, 82% yield). $^1$H NMR (400 MHz, 9:1 CDCl₃:CD₃OD, 25° C.): δ0.810 (3H, t, J=6.9), 1.19 (26 H, br s, W $_{1/2}$=20), 1.44 (4H, complex m), 1.55 (2H, complex m), 2.17 (6H, two overlapping t, J=7.1), 3.79 (2H, d, J=5.1), 6.93 (RCONH, br s, W $_{1/2}$=13.3); $^{13}$C NMR (9:1 CDCl₃CD₃OD): δ14.00, 19.12, 22.63, 25.55, 28.28, 28.33, 28.74, 28.82, 28.88, 29.05, 29.12, 29.17, 29.30, 29.43, 29.59, 31.88, 36.17, 40.35, 42.33, 48.36, 48.57, 48.78, 49.00, 49.21, 49.42, 49.64, 65.28; high-resolution mass spectrum (FAB⁺) calcd. for $C_{27}H_{27}N_2O_2$ (MH⁺): 431.3638 Found: 431.3629.

10,12-pentacosadiynoicphenylalaninamide (PDA-phenylalaninamide)

To a stirring solution of 1.24 g (7.57 mmol) L-phenylalaninamide dissolved in 63.5 mL $CH_2Cl_2$ and 1.5 mL $N(Et)_3$ was slowly added (ca. 1 min) 3.23 g (6.85 mmol) of the PDA-NHS ester from the first protocol. The solution became increasingly cloudy for the next ten minutes. The solution was cooled to 0° C. and allowed to continue stirring overnight in the dark. The methylene chloride solution was extracted with three 100 mL portions of distilled H₂O and then concentrated to dryness under reduced pressure (rotary evaporator). The crude yield for the reaction was 1.89 g (53% yield), and recrystallization from 200 mL of CH₃OH gave 1.82 g of pure product as a white powdery solid (3.49 mmol, 51% yield). $^1$H NMR (400 MHz, CDCL₃, 25° C.): δ0.861 (3H, t, J=7.1), 1.24 (22H, br s W $_{1/2}$=20), 1.34 (4H, complex m), 1.49 (6H, complex m), 2.13 (2H, t, J=7.3), 2.22 (4H, t, J=6.9), 3.05 (2H, dd, J=7.0, 2.2), 4.74 (1H, two overlapping triplets, J=7.1), 5.71 (RCONH, s, W $_{1/2}$=12/6), 6.29 (RCONH, s, W $_{1/2}$=13.1), 6.37 (RCONH, d, J=7.8), 7.29–7.19 (5H, complex m); $^{13}$C NMR (400 MHz CDCl$_3$, 25° C.): δ14.06, 19.14, 19.16, 22.63, 25.46, 28.26, 28.32, 28.72, 28.82, 28.84, 29.03, 29.05, 29.09, 29.29, 29.43, 29.56, 29.58, 29.59, 31.87, 36.42, 38.21, 53.80, 65.22, 65.32, 77.37, 77.58, 126.99, 128.59, 129.24, 136.53, 173.26, 72.43; high-resolution mass spectrum (FAB$^+$) calcd. for C$_{34}$H$_{35}$N$_2$O$_2$ (MH): 521.4107. Found: 521.4125.

10,12-pentacosadiynoicserinamide (PDA-serinamide)

To a stirring of 1.05 g (7.43 mmol) of L-serinamide hydrochloride dissolved in 150 mL CH$_2$Cl$_2$, 50 mL DMSO and 2 mL N(Et)$_3$ was added 4.446 g (9.44 mmol) of the PDA-NHS ester from the first protocol. The solution was cooled to 0° C. and allowed to continue stirring overnight in the dark. The methylene chloride solution was extracted with three 100 mL portions of distilled H$_2$O and then concentrated to dryness under reduced pressure (rotary evaporator). The crude yield for the reaction was 3.14 g (6.81 mmol, 92%). The pentacosadiynoicserinamide compound is particularly susceptible to undesired ultra-violet polymerization. The crude product was dissolved in 100 mL of CHCl$_3$ to give a pinkish solution and then passed through a silica plug to remove polymer contaminant before further purification. The resultant CHCl$_3$ solution was then cooled to 0° C. in an ice bath and treated with 3.26 mmol of CH$_2$N$_2$ dissolved in 3 mL ethyl ether to convert the starting acid and the excess PDA-NHS ester to the methyl ester. Chromatography on silica gel eluting with 65:35:5 hexane/CHCl$_3$/CH$_3$OH afforded 2.119 g (4.61 mmol, 62%) of pure product as a powdery white solid. $^1$H NMR (400 MHz, CDCl$_3$, 25° C.): 0.811 (3H, t, J=7.0) 1.19 (22H, br s, W ½>=10), 1.44 (2H complex m), 1.57 (4H, complex m), 2.17 (6H, two overlapping t, J=7.0), 3.54 (1H, dd, J=11.6, 4.2), 4.12 (1H, d, J=11.3), 4.36 (1H, complex m), 5.35 (RCONH, s, W $_{1/2}$=11.1), 6.51 (RCONH, d, J=6.2), 6.71 (RCONG, s, W ½>=13.1); $^{13}$C NMR (400 MHz CDCl$_3$, 25° C.): δ14.10, 19.14, 19.18, 22.69, 25.49, 28.27, 28.35, 28.72, 28.86, 29.11, 29.34, 29.48, 29.61, 29.63, 29.64, 31.91, 53.12, 53.63, 62.38, 77.21; high-resolution mass spectrum (FAB$^+$) calcd. for C$_{28}$H$_{48}$N$_2$O$_3$ (MH$^+$): 461.3665. Found: 461.3743.

10,12-pentacosadiynoicalaninamide (PDA-alaninamide)

To a stirring solution containing 0.585 g (4.70 mmol) of L-alaninamide hydrochloride dissolved in 50 mL CH$_2$Cl$_2$, 20 mL EtOH and 3 mL N(Et)$_3$ was added 1.14 g (2.41 mmol) of the PDA-NHS ester. The solution was warmed gently to dissolve L-alaninamide hydrochloride salt, and then the reaction mixture was cooled slowly to room temperature and allowed to stir overnight in the dark. The resulting cloudy white solution was extracted with two 150 mL portions of distilled H$_2$O and then extracted with two 50 mL portions of hexane. The organic layer was retained and evaporated to dryness under reduced pressure. Flash chromatography of the resulting blue powder using 12:7:1 CHCL$_3$/HEXANE/CH$_3$OH as the eluent afforded 0.514 g (1.16 mmol, 48%) of pure product as a white chalky solid. $^1$H NMR (400 MHz, CDCl$_3$, 25° C.): δ0.864 (3H, t, J=6.6), 1.24 (26H, br s), 1.38 (3H, d, J=7.0), 1.49 (4H, br m), 1.60 (2H, br dr, J=13.9, 6.9), 2.19 (2H, t, J=8.0), 2.22 (4H, t, J=6.9), 4.53 (1H, m, J=7.2), 5.46 (RCONH, br s, W $_{1/2}$=20), 6.14 (RCONH, br d, J=7.0), 6.37 (RCONH, br s W $_{1/2}$=20). $^{13}$C NMR (400 MHz CD$_3$OD, 25° C.): δ14.09, 18.11, 19.17, 19.19, 22.66, 25.51, 28.28, 28.35, 28.73, 28.85, 28.87, 29.08, 29.12, 29.32, 29.46, 29.59, 29.61, 29.62, 31.90, 36.51, 48.16, 65.32, 77.41, 77.62, 173.19; high-resolution mass spectrum (FAB$^+$) calcd. for C$_{28}$H$_{49}$N$_2$O$_2$ (MH$^+$): 445.3794. Found: 445.3804.

10,12-pentacosadiynamide (PDA-amide)

To a flame dried flask was added 100 mL CH$_2$Cl$_2$ and 0.500 g (1.34 mmol) of PDA. The flask was cooled to 0° C. in an ice bath and the solution purged with nitrogen. To the stirring solution, 0.400 mL (4.68 mmol) of trimethylacetyl chloride (Registry No. 3282-30-2) and 3.7 mL of N(Et)$_3$ were added dropwise. Ammonia was bubbled through the solution at 0° C, for 1 hour and the reaction was stirred under a nitrogen atmosphere for 3 hours. The reaction mixture was filtered through a silica plug. The filtrate was evaporated to dryness and the resulting white powder was recrystallized immediately from 2-propanol to give 0.460 g (1.23 mmol, 92%) of pure product. $^1$H NMR (400 MHz, CDCl$_3$, 25° C.): δ0.866 (3H, t, J=6.7), 1.24 (26H, br s), 1.50 (4H, br m), 1.62 (2H, br m), 2.21 (2H, t, J=8.0), 2.23 (4H, t, J=7.1), 5.42 (2H, br s, W $_{1/2}$=40), $^{13}$C NMR (400 MHz, CDCl$_3$, 25° C.): δ14.67, 19.18, 19.20, 22.67, 25.45, 28.28, 28.36, 28.72, 28.82, 29.09, 29.12, 29.33, 29.46, 29.59, 29.61, 29.63, 31.91, 35.88, 65.20, 77.37, 77.58, 147.89, 177.20; mass spectrum m/z (relative intensity) 748(12), 396(25), 374(M-H$^+$, 100), 307(18), 289(20), 219(38), 428(32), 400(18), 307(20), 289(12), 219(15), 154(100), 136(75), 123(17), 107(30).

B. Incorporation of Functionalized Monomers into Films

The synthesis of the peptide derivatized lipid (PDL) monomers is described in the following scheme. Compound (1) (10,12-PDA) was treated with N-hydroxysuccinimide (NHS) using N,N,1-(3-dimethylaminopropyl)- 3-ethylcarbodiimide (EDCI) as a coupling agent to form the PDA-NHS ester (2) in approximately yield. The PDA-NHS ester (2) was reacted with glycinamide, alaninamide, phenylalaninamide and serinamide to give the peptide derivatized lipids listed in Table 4 (compounds 3a–e). The yields of PDA(alaNH$_2$) and PDA(pheNH$_2$) were approximately 65–70% while the yields of PDA(serNH$_2$) and PDA(glyNH$_2$) were approximately 40–50%.

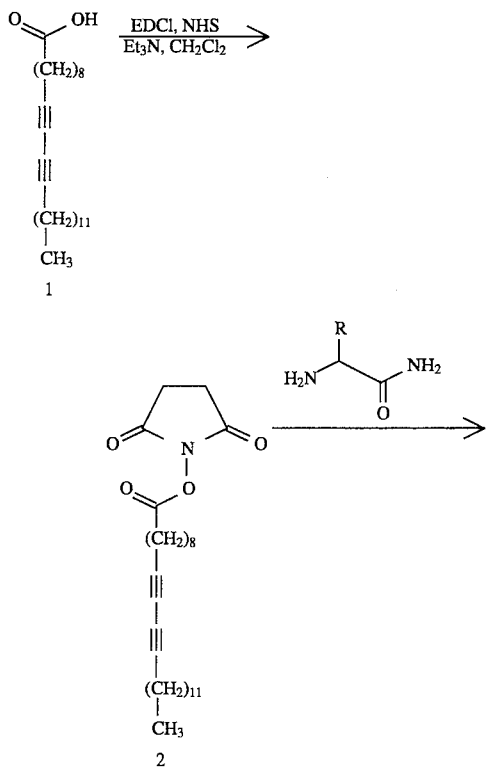

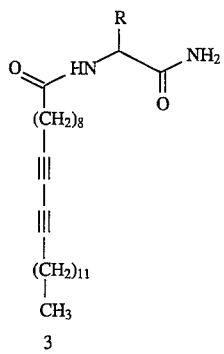

a) (R = H)
b) (R = CH$_3$)
c) (R = —CH$_2\phi$)
d) (R = —CH$_2$OH)

Self-assembled PDL films were formed using a modified Langmuir-Blodgett procedure. The lipids were spread at an air-water interface and were then crystallized by applying a differential cooling gradient along the water surface. The crystalline monolayer film was polymerized with UV irradiation and then transferred onto other surfaces by touching the two surfaces together. A detailed procedure for the formation of a PDA(alaNH$_2$) film is provided below.

The PDA(alaNH$_2$) monomer was dissolved in methylene chloride (CH$_2$Cl$_2$) and hexane (1:1) at a concentration of 5.4 mM as determined by $^1$H NMR spectroscopy using an internal standard. Approximately 20 ul of this solution was spread at an air-water interface using the modified LB film balance described herein. The water layer to which the lipids were applied (i.e., the subphase) was distilled and passed through a Millipore Q purification system until the resistance was greater than 18 Mohm-cm and was heated to approximately 50° C. before the lipid solution was applied to the surface. The subphase was then cooled to approximately 15°–18° C. to induce crystallization of the monolayer, and the crystalline monolayer subsequently polymerized with ultraviolet radiation at 254 nm. PDA(glyNH$_2$), PDA(serNH$_2$) and PDA(pheNH$_2$) were spread in a solvent mixture of CH$_2$Cl$_2$:CH$_3$OH (1:1) at a concentration of approximately 1 mg/mL (e.g., 20 uM). The subphase temperature for spreading PDA(glyNH$_2$) and PDA(serNH$_2$) was 60° C. and the polymerization temperature was 15° C.; the subphase temperature for spreading PDA(pheNH$_2$) was 70° C. and the polymerization temperature was 20° C.

The resulting peptide films were transferred to hydrophobic glass slides that were prepared by a modification of the Sagiv method using octadesyltrichlorosilane as a silylating agent. The peptide derivatized surfaces were characterized by contact angle measurements, X-ray photoelectron spectroscopy, ellipsometry and fluorescence microscopy. Table 4 gives the contact angle measurements for these surfaces and FIG. 5 shows a typical fluorescence micrograph and XPS depth profile for the PDA(alaNH$_2$) film.

Contact Angle Measurements of PDL Films

| Entry | R | Contact Angles |
|---|---|---|
| 1 | H (3a) | 80° |
| 2 | CH$_3$ (3b) | 55° |
| 3 | CH$_2$OH (3c) | 55° |
| 4 | CH$_2$C$_6$H$_5$ (3d) | 90° |

Figure 5A:
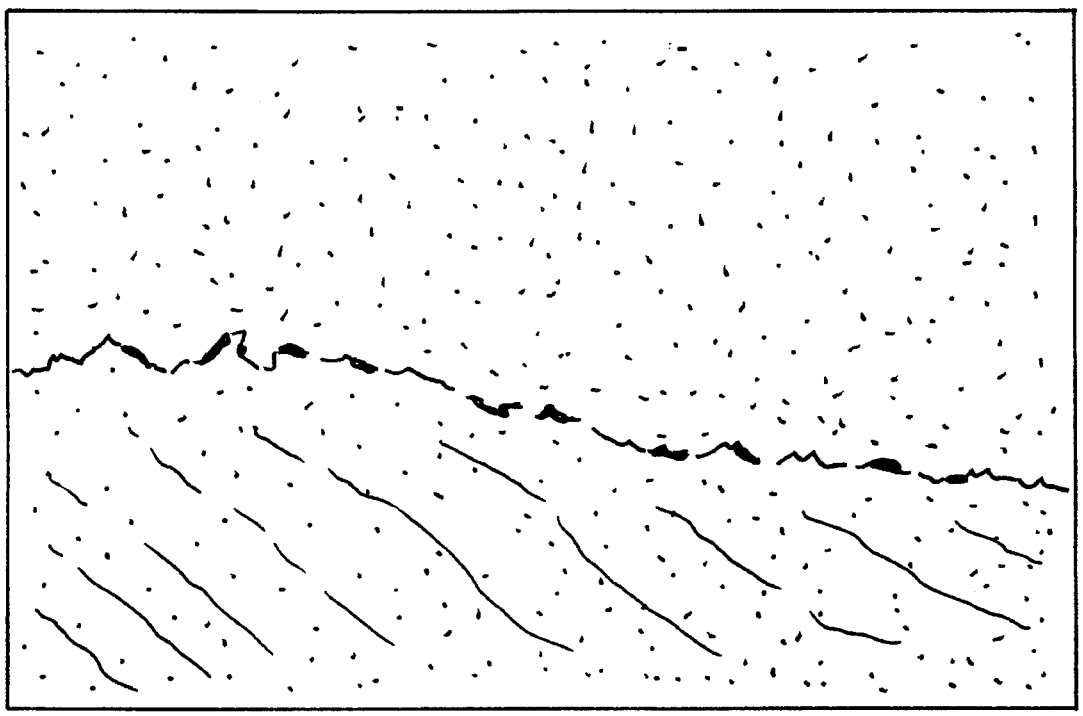
FIG. 5 shows the fluorescence image of a polymerized film (FIG. 5A) along with its XPS spectrum (FIG. 5B). The XPS spectrum provides evidence of the presence of the ligand group, the ligand attachment group, the linker and the surface attachment group.

The fluorescence micrograph in FIG. 5A shows the gross morphology of the surface including the presence of the crystals, the large crystal boundries and small holes in the film that are approximately 1–100 uM in length which makes the film porous. These holes may be due to the contraction of the film that occurs during the polymerization reaction. The average contraction for simple diacetylene monomers is 0.1–0.25 Å, a number that when multiplied by the molecules on the surface (approximately $10^{15}$/cm) easily accounts for the observed spaces between the film.

Figure 5B:
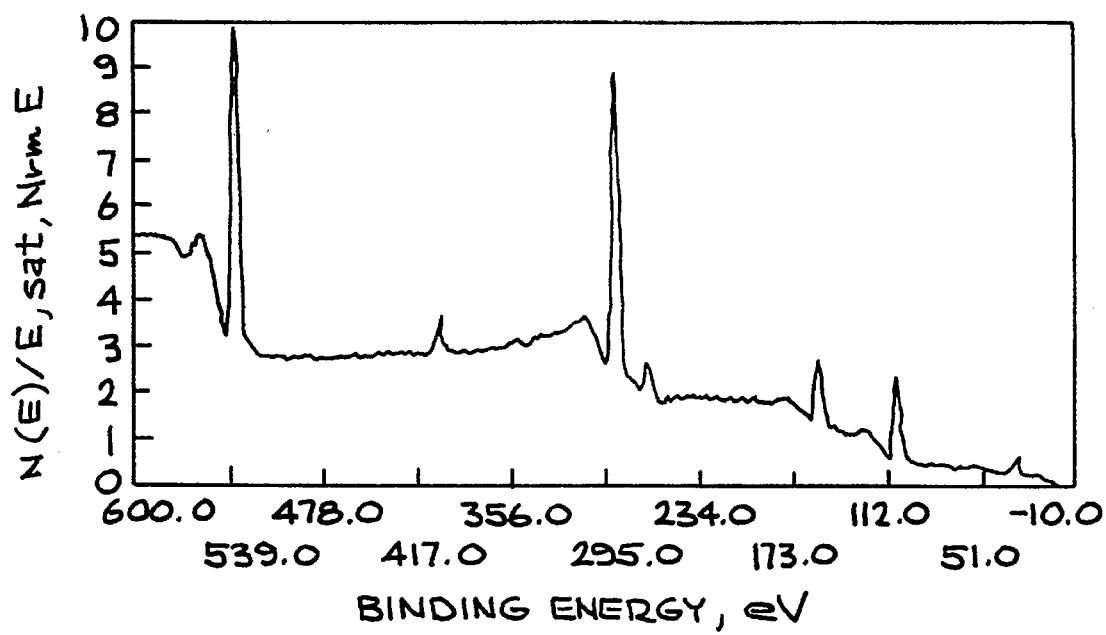

The XPS spectrum in FIG. 5B shows the presence of silicon, nitrogen, carbon and oxygen on the surface. The high resolution carbon profile also shows the presence of the carbonyl groups of the amide bond and the heterosubstituted carbon on the peptide. The XPS depth profile gives a strong and steady nitrogen signal and a relationship of intensity of the carbon and silicon signal to the take-off angle. This data is consistent with the amino acid head group being orientated at the surface of the film and the carbon chain extending from the amino acid head group towards the silicon surface. Finally, an ellipsometric measurement of 50 Å and a contact angle measurement of 55 degrees are also consistent with proposed orientation of the film. The elliposometric measurement of underivatized OTS treated glass is 25 Å and the contact angle is 115 degrees.

PDA(glyNH$_2$) and PDA(serNH$_2$) gave similar results as that for PDA(alaNH$_2$). The contact angle measurements for PDA(glyNH$_2$) was 45 degrees and that for PDA(glyNH$_2$) was 35 degrees indicating the correct orientation of the amino acid head group on the surface. The XPS data and the elliposmetic measurements were also consistent with this orientation. PDA(glyNH$_2$) showed a film thickness of 48 Å and PDA(serNH$_2$) showed a film thickness of 54 Å. The XPS depth profile showed the same trend as the PDA(alaNH$_2$) film, a strong surface nitrogen peak, a high resolution carbon showing the presence of the carbonyl group and heteroatom substituted carbons on the peptide and a relationship between the take-off angle and the silicon and carbon peaks.

In the case of PDA(pheNH$_2$), however, the contact angle was 98 degrees and the XPS measurements did not show the strong surface nitrogen and carbonyl peaks and the take-off angle dependence of carbon and silicon. The ellipsometry measurements were also inconsistent with the film orientations such that the head groups extend 30 Å away from the OTS treated glass slide. From this data one concludes that the PDA(pheNH$_2$) monomer lies down flat on the water surface prior to polymerization. This orientation is probably due to the hydrophobic interactions of the phenyl head group with the hydrophobic surface. Similar results have also been observed with the PDA(alaNH$_2$) films when the amount of material applied to the surface is not sufficient to form a monolayer. The Van der Waals interactions of the lipid with the subphase surface is an attractive interaction and can orientate the monomers parallel to the surface until a critical concentration of the lipid is achieved at which point the material rearranges to form a film orientated with the head groups away from the surface.

In summary, a new and simple method for the construction of molecular films that can be used to orientate peptides and other ligands on a surface has been presented. It has been shown that the amino acid head groups in the peptide monomers can strongly influence the interfacial properties of a material and determine the orientation of the film.

Other modifications of the above-described embodiments of the invention that are obvious to those of skill in the art of materials science, molecular biology and related disciplines are intended to be within the scope of the following claims.

We claim:
1. A monomer capable of molecular self-assembly selected from the group consisting essentially of:
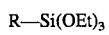
wherein R is
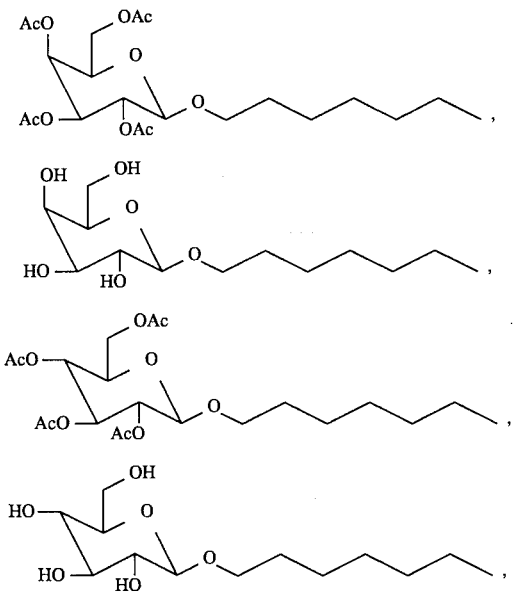
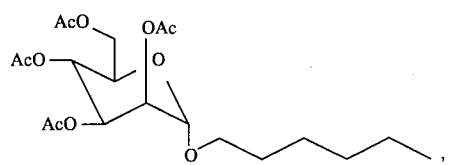
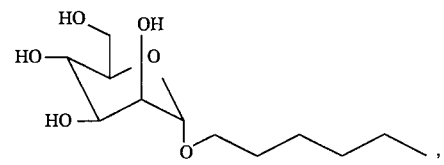
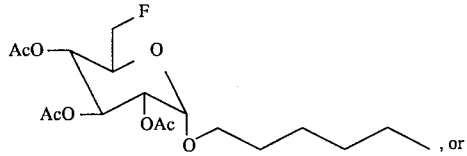
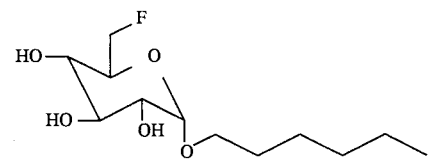
* * * * *